US006440944B2

(12) United States Patent
Bruder et al.

(10) Patent No.: US 6,440,944 B2
(45) Date of Patent: *Aug. 27, 2002

(54) METHODS OF ADMINISTERING ADENOVIRAL VECTORS

(75) Inventors: Joseph T. Bruder, Frederick; Imre Kovesdi, Rockville, both of MD (US)

(73) Assignee: GenVec, Inc., Gaithersburg, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/174,508

(22) Filed: Oct. 16, 1998

(51) Int. Cl.[7] ............... A61K 48/00; A61K 35/00; A61K 39/235; C12N 15/63

(52) U.S. Cl. ............... 514/44; 435/320.1; 435/455; 435/69.1; 435/69.6; 424/93.1; 424/199.1; 424/233.1

(58) Field of Search ............ 514/44; 424/93.1, 424/184.1, 199.1, 204.1, 233.1; 435/320.1, 455, 456, 69.1, 69.6

(56) References Cited

U.S. PATENT DOCUMENTS

| 5,585,362 A | | 12/1996 | Wilson et al. ............... 514/44 |
| 5,830,879 A | * | 11/1998 | Isner ............... 514/44 |
| 5,981,275 A | * | 11/1999 | Armentano et al. ...... 435/320.1 |

FOREIGN PATENT DOCUMENTS

| WO | WO 95/34671 | | 12/1995 |
| WO | WO 96/40272 A1 | | 12/1996 |
| WO | WO 97/06826 A1 | | 2/1997 |
| WO | WO 98/35028 A3 | | 8/1998 |
| WO | WO 98/35028 A2 | | 8/1998 |

OTHER PUBLICATIONS

Christ M et al. Immunology Letters 57:19–25, 1997.*
Michou A et al. Gene Therapy 4:473–482, 1997.*
Yang Y et al. Human Molecular Genetics 11:1703–1712, 1996.*
Mack CA et al. Human Gene Therapy 8: 99–1–9, 1997.*
Gilgenkrantz H et al. 6:1265–1274, 1995.*
Barr et al., *Gene Ther.*, 2, 151–155 (1995).
Bennett et al., *Hum. Gene Ther.*, 7, 1763–1769 (1996).
Berkner et al., *J. Virol.*, 61, 1213–1220 (1987).
Curiel et al., *Hum. Gene Ther.*, 3, 147–154 (1992).
Davidson et al., *J. Virol.*, 61, 1226–1239 (1987).
Ilan et al., *Proc. Natl. Acad. Sci. USA*, 94, 2587–2592 (1997).
Jaffee et al., *Nature Genet.*, 1, 372–78 (1992).
Kay et al., *Nature Genet.*, 11, 191 (1995).
Lee et al., *Hum. Gene Ther.*, 7, 2273 (1996).
Li et al., *Cardiovascular Res.*, 30, 97–105 (1995).
Mack et al., *Hum. Gene Ther.*, 8, 99–109 (1997).
Mansour et al., *Mol. Cell Biol.*, 6, 2684–2694 (1986).
Michou et al., *Gene Ther.*, 4, 473–482 (1997).
Svensson et al., *Hum. Gene Ther.*, 8, 1797–1806 (1997).
Tripathy et al., *Nature Med.*, 2, 545–550 (1996).
Wilson et al., *Nature Med.*, 1, 887–889 (1995).
Yang et al., *J. Virol.*, 69, 2004 (1995).
Yang et al., *J. Virol.*, 70, 6370 (1996).
Yang et al., *Human Molecular Genetics*, 5 (11), 1703–1712 (1996).

* cited by examiner

*Primary Examiner*—Dave T. Nguyen
*Assistant Examiner*—Ram R. Shukla
(74) *Attorney, Agent, or Firm*—Leydig, Voit & Mayer, Ltd.

(57) ABSTRACT

The present invention provides methods for administering an adenoviral gene transfer vector comprising an exogenous gene to an animal. One method involves utilizing systemic neutralizing antibodies to neutralize the adenoviral gene transfer vector outside a targeted muscle. Another method involves the repeat administration of an adenoviral gene transfer vector to a skeletal muscle.

15 Claims, 1 Drawing Sheet

METHODS OF ADMINISTERING ADENOVIRAL VECTORS

TECHNICAL FIELD OF THE INVENTION

The present invention relates to methods useful in the administration of gene products to animals using adenoviral vectors.

BACKGROUND OF THE INVENTION

Modified viruses have proven convenient vector systems for investigative and therapeutic gene transfer applications, and adenoviral vector systems present several advantages for such uses. Adenoviruses are generally associated with benign pathologies in humans, and the 36 kb of the adenoviral genome has been extensively studied. Adenoviral vectors can be produced in high titers (e.g., about $10^{13}$ pfu), and such vectors can transfer genetic material to nonreplicating, as well as replicating, cells (in contrast with, for example, retroviral vectors which only transfer genetic material to replicating cells). The adenoviral genome can be manipulated to carry a large amount of exogenous DNA (up to about 8 kb), and the adenoviral capsid can potentiate the transfer of even longer sequences (Curiel et al., *Hum. Gene Ther.*, 3, 147–154 (1992)). Additionally, adenoviruses generally do not integrate into the host cell chromosome, but rather are maintained as a linear episome, thus minimizing the likelihood that a recombinant adenovirus will interfere with normal cell function. Aside from being a superior vehicle for transferring genetic material to a wide variety of cell types, adenoviral vectors represent a safe choice for gene transfer, a particular concern for therapeutic applications.

A variety of recombinant adenoviral vectors have been described. Most of the vectors in use today derive from the adenovirus serotype 5 (Ad5), a member of subgroup C. An exogenous gene of interest typically is inserted into the early region 1 (E1) of the adenovirus. Disruption of the E1 region decreases the amount of viral proteins produced by both the early regions (DNA binding protein) and late regions (penton, hexon, and fiber proteins), preventing viral propagation. These replication deficient adenoviral vectors require growth in either a complementary cell line or in the presence of an intact helper virus, which provides, in trans, the essential E1 functions (Berker et al., *J. Virol.*, 61, 1213–1220 (1987); Davidson et al., *J. Virol.*, 61, 1226–1239 (1987); Mansour et al., *Mol. Cell Biol.*, 6, 2684–2694 (1986)). More recently, adenoviral vectors deficient in both E1 and the early region 4 (E4) have been used to substantially abolish expression of viral proteins. In order to insert the larger genes (up to 8 kb) into the adenoviral genome, adenoviral vectors additionally deficient in the nonessential early region 3 (E3) are used. Multiply deficient adenoviral vectors are described in published PCT patent application WO 95/34671.

One limitation of adenoviral vector systems is the ability of the adenoviral vector to transduce a wide variety of proliferating and quiescent cells (Michou et al., *Gene Ther.*, 4, 473–482 (1997)). This ability, while a benefit in transducing the target area, is a limitation when the adenoviral vector "leaks" out of the targeted area and transduces other cells it contacts. Tranduction of the surrounding cells is a severe problem when the gene product encoded by the adenoviral vector is harmful, toxic, or otherwise undesirable with respect to these non-targeted areas.

Another limitation of the adenoviral vector system is the cellular and humoral immune response generated within the host animal. Initial administration elicits a reaction from both $CD8^+$ and $CD4^+$ T cell lymphocytes which eliminate virus infected cells within 28 days after infection, limiting the duration of the transgene expression. In addition, neutralizing antibodies produced by B lymphocytes in cooperation with $CD4^+$ cells inhibit the effectiveness of a repeat administration of the adenoviral vector. Proliferation and specificity of the antibodies is achieved through interactions between the adenoviral vector, B-cell surface immunoglobulins and activated $CD4^+$ surface proteins (particularly CD40Li, which binds CD40 on the surface of the B cell) (Yang et al., *J. Virol.*, 69, 2004 (1995)).

Attempts to circumvent the humoral immune response to allow repeat administration of the adenoviral vector have met with limited success. These attempts have been focused in two areas, immunosuppression and alteration of the adenoviral vector. Several groups have experimented with various immunosuppressant drugs or antibodies specific for $CD4^+$, CD40 ligand, or CTLA4Ig to reduce the adenovirus-specific humoral immune response (Lee et al., Hum. Gene Ther., 7, 2273 (1996) ($CD4^+$); Yang et al.,*J. Virol.*, 70, 6370 (1996) (CD40 ligand); Kay et al., *Nature Gen.*, 11, 191 (1995) (CTLA4Ig)). Although some of these results have been encouraging, there is a substantial risk associated with systemic immune suppression in a clinical setting.

In another study, subretinal administration of an adenoviral vector containing the bacterial β-galactosidase gene resulted in minimal circulating antibodies specific to the adenoviral vector. This was most likely a reflection of the immune privileged status of the retina. Although there was minimal retinal toxicity to the adenovirus, several of the animals injected developed localized granulomatous infiltrate at the injection site (Bennett et al., *Hum. Gene Ther.*, 7, 1763–1769 (1996)). Subretinal administration is not an option for many applications where adenoviral vectors are employed.

Alteration of the adenoviral vector is time consuming and has not been entirely successful in sufficiently attenuating the immune response. Limited readministration of the adenoviral vector has been accomplished when adenoviral vectors of different serotypes within the same subgroup are used; however, persistence of expression of the transgene was not comparable to the initial administration (Mack et al., *Hum. Gene Ther.*, 8, 99–109 (1997)).

Accordingly, there is a need for improved methods of administering adenoviral vectors to animals, particularly, to prevent leakage of the adenoviral vector from the target area and to circumvent the humoral immune response elicited by adenoviral vectors. The present invention provides such methods. This and other advantages of the present invention, as well as additional inventive features, will be apparent from the description of the invention provided herein.

BRIEF SUMMARY OF THE INVENTION

The present invention provides a method of targeting a gene product in a particular muscle of an animal. The method utilizes systemic neutralizing antibodies to neutralize an adenoviral gene transfer vector containing an exogenous gene outside the particular muscle. The adenoviral gene transfer vector is administered such that the exogenous gene is expressed and the gene product is produced only in the particular muscle of administration.

The present invention further provides a method of producing a gene product in a skeletal muscle of an animal. The method comprises a first intramuscular administration of an adenoviral vector to the skeletal muscle of an animal, and a second administration of an adenoviral gene transfer vector containing an exogenous gene encoding a gene product. Administration is such that the exogenous gene is expressed and the gene product is produced in the skeletal muscle of the animal.

The invention may best be understood with reference to the accompanying drawings and in the following detailed description.

DETAILED DESCRIPTION OF THE INVENTION

Figure 1:
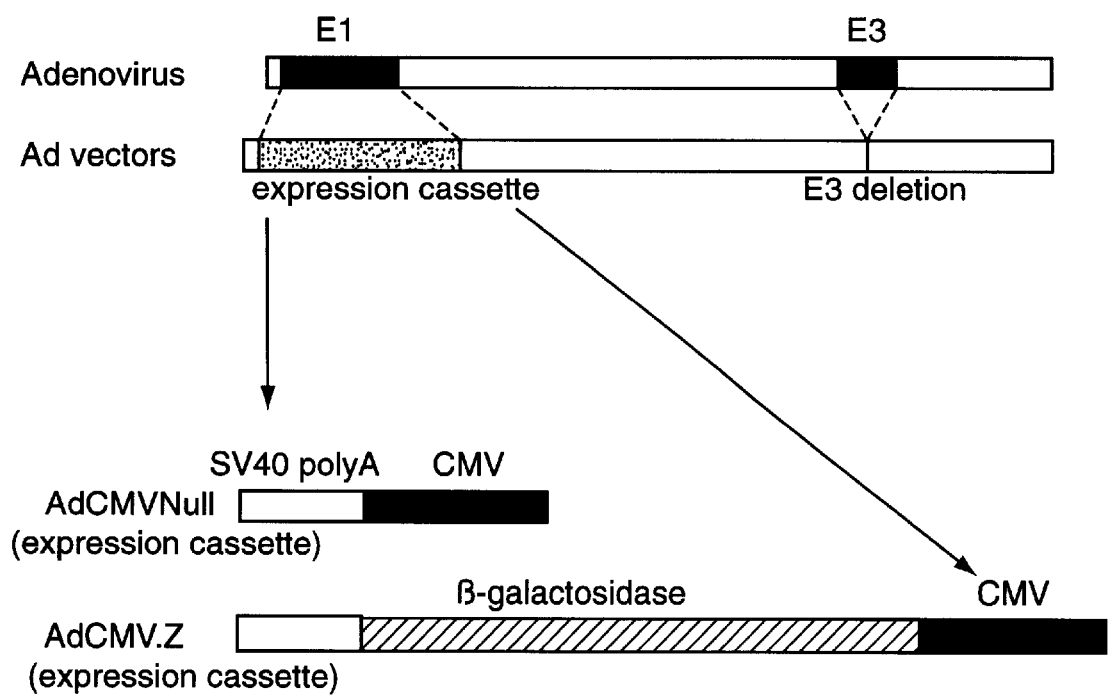
FIG. 1 is a schematic diagram depicting the original adenovirus used to derive the adenoviral vectors AdCMVNull and AdCMV.Z, the regions of addition and deletion of the original adenovirus, and the expression cassettes of the adenoviral vectors AdCMVNull and AdCMV.Z.

The present invention provides methods useful in the administration of gene products to animals using adenoviral gene transfer vectors. The ability to target an adenoviral vector and to repeatedly administer a therapeutic adenoviral vector in a clinical setting is useful in improving treatment efficacy and in enabling the treatment of diseases. This invention provides a method to limit the infection of non-target tissue following administration of an adenoviral vector to a particular muscle of an animal. The vector targeting potential is useful for cardiac, particularly, endocardial, administration, as the risk of misinjection of the adenoviral vector is high. As adenoviral vectors cannot be readministered systemically, the present invention also provides a method for repeat administration of an adenoviral gene transfer vector comprising an exogenous gene to the skeletal muscle of an animal.

The term "exogenous gene", as it is used herein, refers to any gene in an adenoviral gene transfer vector which is not native to the adenovirus which comprises the adenoviral vector. The gene includes a nucleic acid sequence encoding a gene product operably linked to a promoter. Any portion of the gene can be non-native to the adenovirus which comprises the adenoviral vector. For example, the gene can comprise a non-native nucleic acid sequence encoding a gene product which is operably linked to a native promoter. It should be appreciated that the exogenous gene can be any gene encoding an RNA or protein of interest to the skilled artisan. Therapeutic genes, genes encoding a protein that is to be studied in vitro and/or in vivo, genes encoding antisense RNA's, and modified viral genes are illustrative of possible exogenous genes.

The term "adenoviral gene transfer vector", as it is used herein, refers to any replication incompetent adenoviral vector with an exogenous gene encoding a gene product inserted into its genome. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art.

In one embodiment, the present invention provides a method of targeting a gene product to a muscle of an animal using an adenoviral gene transfer vector containing an exogenous gene encoding a gene product. Systemic neutralizing antibodies to a particular adenoviral gene transfer vector are first induced in the animal. The adenoviral vector is then administered to a particular muscle of an animal such that the exogenous gene encoded by the adenoviral vector is expressed and the gene product produced in the particular muscle of the animal. In addition, the adenoviral vector is neutralized outside the muscle of administration.

The present invention can be practiced with any suitable animal, preferably a mammal, more preferably, a human. Additionally, the adenoviral vector can be administered to any suitable muscle of the animal; however, it is preferably administered to the heart.

Any suitable method can be used to induce systemic neutralizing antibodies to the adenoviral vector. Desirably, an antigen is administered to the animal. This antigen can be the adenoviral gene transfer vector, but preferably, it is an identical adenoviral vector, except without an exogenous gene (an AdCMVNull vector, an example of which can be found in FIG. 1). The antigen can also be administered by any suitable method. Depending on the antigen, administration can be to any suitable area of the animal. In order to induce the systemic neutralizing antibodies, the antigen can be administered any number of suitable times, e.g., once, twice, or more.

Using the AdCMVNull vector administration, the antigen can be administered systemically (rather than to the target muscle) to prevent any damage to the particular muscle. Systemic administration can be accomplished through intravenous injection, either bolus or continuous, or any other suitable method. An added benefit of systemic administration is that it requires a much smaller amount of antigen to produce the same levels of circulating antibodies as administration to any muscle of the animal.

Administration of the antigen produces circulating neutralizing antibodies. While not wishing to be bound by any particular theory, it is believed that when the adenoviral gene transfer vector is administered to the particular muscle of the animal, some of the adenoviral particles escape the muscle. These adenoviral particles are then neutralized by the antibodies circulating throughout the animal such that significantly less (and preferably substantially no) gene product is produced outside the particular muscle. The amount of exogenous gene product produced outside the area of administration is preferably at least 10% less (more preferably at least 50% less, and most preferably at least 80% less) than production of the gene product outside the particular muscle of administration in a naive animal, which does not have circulating neutralizing antibodies to the adenoviral gene transfer vector.

Neutralization of adenoviral particles outside of the particular muscle prevents production of the exogenous gene carried in the adenoviral gene transfer vector. This is extremely useful in situations where the exogenous gene is harmful, or toxic, to the animal when present in areas other than the particular muscle of administration. An example of this is vascular endothelial growth factor (VEGF protein), which mediates vascular growth. While vascular growth is desirable in the heart to repair damaged cardiac muscle, growth outside the heart can lead to severe problems, including blindness, and increased aggressiveness of tumor cells.

In another embodiment, the present invention provides a method of producing a gene product in a skeletal muscle. An adenoviral vector is first administered to the skeletal muscle of an animal. An adenoviral vector containing an exogenous gene encoding a gene product is then administered to the same skeletal muscle such that the exogenous gene is expressed and the gene product is produced in the skeletal muscle. Any suitable animal can be used; however, preferably, the animal is a mammal, more preferably, a human.

After the second or subsequent administration of the adenoviral gene transfer vector, production of the gene product in the muscle of the animal is desirably at least 1% of (such as at least 10% of, preferably at least 50% of, more preferably at least 80% of, and most preferably, substantially the same as) production of the gene product after a first or preceding administration with the same adenoviral gene transfer vector containing the exogenous gene encoding the gene product. While not wishing to be bound by any particular theory, it is believed that the level of gene product produced in the skeletal muscle of an animal after the second or subsequent administration to the muscle can be substantially similar to that of the first or preceding administration because neutralizing antibodies, which are produced by the first or preceding administration, cannot readily penetrate the muscle and destroy the adenoviral gene transfer vector. This holds true even when the neutralizing antibody response is boosted with two or more initial administrations before the final or subsequent intramuscular administration of the adenoviral gene transfer vector containing the exogenous gene encoding the gene product.

To facilitate the administration of adenoviral vectors, they can be formulated into suitable pharmaceutical compositions. Generally, such compositions include the active ingredient (i.e., the adenoviral vector) and a pharmacologically acceptable carrier. Such compositions can be suitable for delivery of the active ingredient to a patient for medical application, and can be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention can be formulated in a conventional manner using one or more pharmacologically or physiologically acceptable carriers comprising excipients, as well as optional auxiliaries which facilitate processing of the active compounds into preparations which can be used pharmaceutically. Proper formulation is dependent upon the route of administration chosen. Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

The present inventive methods are useful in the context of the treatment of animals, e.g., medical treatment. In addition, the present inventive methods are useful in the production of gene products, e.g., in vivo protein production (which can entail subsequent protein recovery) as well as in research, e.g., investigation of gene expression, adenoviral targeting, and the like.

EXAMPLE

The present invention is further described in the following example. This example serves only to illustrate the invention and is not intended to limit the scope of the invention in any way.

This example illustrates use of the present inventive method of targeting production of a gene product to a particular muscle in an animal, as well as the present inventive method of repeat administration to produce a gene product in a skeletal muscle of an animal. In particular, systemic neutralizing antibodies to an adenoviral vector were induced in an animal, and then the adenoviral vector comprising an exogenous gene encoding a gene product was administered to a particular muscle of the animal such that the exogenous gene was expressed and the gene product was produced in the particular muscle of the animal. In addition, the adenoviral vector was neutralized outside of the particular muscle of the animal such that there was limited expression of the exogenous gene resulting in production of the gene product outside of the particular muscle of the animal.

For the purposes of this experimental work, C57B16 mice were used as the test animals because their immune system is able to recognize adenoviral vectors as foreign antigens and mount a sufficient immune response to destroy the adenoviral vectors, thereby preventing expression of an exogenous gene forming a part of the adenoviral vector. The mice were separated into three groups. Systemic neutralizing antibodies were induced in the mice of group 1 with an adenoviral vector which did not contain an exogenous gene encoding a gene product (AdCMVNull). A similar adenoviral vector (AdCMV.Z), with a gene expression cassette encoding a reporter gene product (i.e., a gene product that could be readily detected), was administered to the mice of groups 1 and 2 to determine whether production of the reporter gene product β-galactosidase (β-gal) was limited to the right gastrocnemius muscle or could be detected in other areas of the mice, particularly the liver inasmuch as adenoviral vectors are known to localize in the liver after entering the bloodstream of an animal (Jaffee et al., Nat. Genet., 1, 372–78 (1992)). The mice of group 2 were treated as a naive group. Only the adenoviral vector AdCMV.Z, with a gene expression cassette encoding the reporter gene product β-gal, was administered intrajugularly to the mice of group 2, i.e., no adenoviral vector was administered to induce systemic neutralizing antibodies in the mice before the administration of the adenoviral vector AdCMV.Z. The mice of group 2 otherwise were treated in the same manner as the mice of group 1. Finally, a control group, group 3, which did not receive any administration of adenoviral vectors, was included.

The AdCMVNull vector was a replication-deficient adenoviral vector with deletions in the E1 and E3 regions. An expression cassette was inserted in the E1-deleted region of the adenoviral vector that included an SV40 polyA sequence and a cytomegaloviral promoter (CMV). The AdCMVNull vector is depicted in FIG. 1.

The AdCMV.Z vector was also a replication-deficient adenoviral vector similar to the AdCMVNull vector, except that the expression cassette included a nucleic acid sequence encoding the reporter gene product β-gal operably linked to the CMV promoter, from left to right, relative to the viral vector. The AdCMV.Z vector is also depicted in FIG. 1.

The protocol for administration of the AdCMVNull and AdCMV.Z vectors to the mice of the two groups was as follows: the mice of group 1 were immunized with an intramuscular injection of $1\times10^{10}$ pu of AdCMVNull on day 1 of the experiment, and received a subsequent intramuscular injection of 1×10^10 pu of AdCMV.Z on day 14. The mice of group 2 (the naive mice) received an injection of 1×10^10 pu of AdCMV.Z on day 14. The mice of group 3 did not receive any injections.

On day 15, the mice in all three groups were sacrificed. The β-gal activity in the mice was determined in the liver and right gastrocnemius muscle. Neutralizing antibody titers also were determined in the mice. The results of these analyzes are set forth below in Table 1.

TABLE 1

| | β-galactosidase Activity (RLU/mg protein) | | Neutralizing Antibodies |
|---|---|---|---|
| | Right Gastrocnemius Muscle | Liver | (reciprocal dilution) |
| Group 1 (AdCMVNull) | $1.4447 \times 10^6$ | $8.0697 \times 10^3$ | 32 |
| Group 2 (Naive) | $4.0748 \times 10^6$ | $5.2022 \times 10^6$ | 1.0 |
| Group 3 (Control) | $1.0683 \times 10^4$ | $7.898 \times 10^3$ | n/a |

As is apparent from the experimental results set forth above, the mice in the first two groups had essentially the same levels of β-gal activity in the right gastrocnemius muscle, about $10^6$ RLU/mg. The mice of group 3 (the control group) had a β-gal activity level of about $10^4$ RLU/mg. The results demonstrate that there was gene expression in the targeted muscle, even in the mice of group 1, which were the subject of the repeat administration. Moreover, the mice of group 1, in which systemic neutralizing antibodies were induced, had significantly less β-gal activity in the liver, about $10^4$ (or a hundred-fold less than measured in the target muscle and approximately the same as the control), thereby demonstrating that there was localization of the targeted gene product to the targeted muscle in accordance with the present invention. In distinct contrast, the mice of group 2, in which neutralizing antibodies were not induced, had essentially the same level of β-gal activity in the liver, about $10^6$ RLU/mg, as in the targeted muscle, thereby indicating that in the absence of the present inventive method, when there is undesirable leaking of the adenoviral vector outside the targeted muscle, there is widespread production of the gene product of interest.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the claims below.

What is claimed is:

1. A method of administering a therapeutic gene product to a particular skeletal muscle of a mammal, which method comprises: (a) inducing in the mammal systemic neutralizing antibodies to a replication-incompetent adenoviral gene transfer vector by systemically or intramuscularly administering an antigen that will induce systemic neutralizing antibodies to the replication-incompetent adenoviral gene transfer vector, and (b) intramuscularly administering the replication-incompetent adenoviral gene transfer vector comprising a therapeutic gene encoding a therapeutic gene product to the particular skeletal muscle of the mammal such that the therapeutic gene is expressed and the therapeutic gene product is produced in the particular skeletal muscle of the mammal, whereby the therapeutic gene product is administered to the particular skeletal muscle of the mammal to produce a therapeutic benefit in the mammal and the replication-incompetent adenoviral gene transfer vector is neutralized outside of the particular skeletal muscle of the mammal, wherein, when the systemic neutralizing antibodies are induced in (a) by intramuscular administration of an antigen that will induce systemic neutralizing antibodies to the replication-incompetent adenoviral gene transfer vector, the antigen is the same as the adenoviral gene transfer vector, except that it does not contain the therapeutic gene encoding the therapeutic gene product.

2. The method of claim 1, wherein the mammal is a human.

3. The method of claim 1, wherein the antigen is the same as the adenoviral gene transfer vector, except that it does not contain the therapeutic gene encoding the therapeutic gene product.

4. The method of claim 1, wherein the antigen is the same as the adenoviral gene transfer vector.

5. The method of claim 1, wherein the neutralizing of the adenoviral gene transfer vector outside the particular skeletal muscle of the mammal is a result of the presence of the neutralizing antibodies.

6. The method of claim 1, wherein the neutralizing of the adenoviral gene transfer vector outside the particular skeletal muscle of the mammal one day after administration is such that the production of the therapeutic gene product is at least 90% less than the production of the therapeutic gene product outside the particular skeletal muscle of a naive animal of the same species as the animal one day after administration of the adenoviral gene transfer vector.

7. The method of claim 6, wherein said neutralizing of said adenoviral gene transfer vector outside said particular muscle of said animal is such that the production of the therapeutic gene product is at least 99% less than the production of the therapeutic gene product outside said particular muscle of a naive mammal of the same species as the mammal after administration of the adenoviral gene transfer vector.

8. The method of claim 7, wherein said neutralizing of the adenoviral gene transfer vector outside the particular skeletal muscle is such that the production of the therapeutic gene product is at least 99.9% less than the production of therapeutic gene product outside the particular skeletal muscle of a naive animal of the same species as the mammal after administration of the adenoviral gene transfer vector.

9. A method of producing a therapeutic gene product in a skeletal muscle of a mammal to produce a therapeutic benefit to the mammal, which method comprises: (a) administering an adenoviral vector to the skeletal muscle of the mammal, and (b) at least seven days after the administration directly administering a replication-incompetent adenoviral gene transfer vector comprising a gene encoding a therapeutic gene product to the skeletal muscle of the mammal such that the gene is expressed and the therapeutic gene product is produced in the skeletal muscle of the mammal to produce a therapeutic benefit of the mammal, wherein, the adenoviral vector of step (a) is the same as the adenoviral gene transfer vector of step (b), except that it does not contain the therapeutic gene encoding the therapeutic gene product.

10. The method of claim 9, wherein the therapeutic gene product is a vascular endothelial growth factor, and the therapeutic benefit is the induction of vascular growth.

11. The method of claim 9, wherein the mammal is a human.

12. The method of claim 9, wherein production of said gene product in the skeletal muscle of the mammal one day after the administration of the adenoviral gene transfer vector comprising the gene encoding the therapeutic gene product is at least 10% of production of the therapeutic gene product in the skeletal muscle of a naive mammal of the same species as the mammal one day after administration of the adenoviral gene transfer vector comprising the gene encoding the therapeutic gene product.

13. The method of claim 12, wherein production of said gene product in the skeletal muscle of the mammal one day after the administration of the adenoviral gene transfer vector comprising the gene encoding the therapeutic gene product is at least 50% of production of the therapeutic gene product in the skeletal muscle of a naive mammal of the same species as the mammal one day after administration of the adenoviral gene transfer vector comprising the gene encoding the therapeutic gene product.

14. The method of claim 13, wherein production of said gene product in the skeletal muscle of the mammal one day after the administration of the adenoviral gene transfer vector comprising the gene encoding the therapeutic gene product is at least 80% of production of the therapeutic gene product in the skeletal muscle of a naive mammal of the same species as the mammal one day after administration of the adenoviral gene transfer vector comprising the gene encoding the therapeutic gene product.

15. The method of claim 14, wherein production of said gene product in the skeletal muscle of the mammal one day after the administration of the adenoviral gene transfer vector comprising the gene encoding the therapeutic gene product is the same or substantially the same as production of the therapeutic gene product in the skeletal muscle of a naive mammal of the same species as the mammal one day after administration of the adenoviral gene transfer vector comprising the gene encoding the therapeutic gene product.

* * * * *